United States Patent [19]

Paoletti et al.

[11] Patent Number: 4,622,847
[45] Date of Patent: Nov. 18, 1986

[54] APPARATUS FOR MEASURING THE RATE OF ERYTHROSEDIMENTATION OF THE BLOOD

[75] Inventors: Sergio Paoletti; Francesco Leopardi, both of Milan, Italy

[73] Assignee: L.P. Italiana S.p.A., Italy

[21] Appl. No.: 540,601

[22] Filed: Oct. 7, 1983

[30] Foreign Application Priority Data

Nov. 5, 1982 [IT] Italy .............................. 24096 A/82

[51] Int. Cl.$^4$ .......................................... G01N 15/04
[52] U.S. Cl. ..................................................... 73/61.4
[58] Field of Search ......................................... 73/61.4

[56] References Cited

U.S. PATENT DOCUMENTS

| | | | |
|---|---|---|---|
| 3,373,601 | 3/1968 | Monn | 73/61.4 |
| 3,660,037 | 5/1972 | Sokol | 73/61.4 X |
| 3,910,103 | 10/1975 | Rose | 73/61.4 |
| 4,197,735 | 4/1980 | Munzer et al. | 73/61.4 |
| 4,353,246 | 10/1982 | Farber et al. | 73/61.4 |

FOREIGN PATENT DOCUMENTS

| | | | |
|---|---|---|---|
| 1169164 | 4/1964 | Fed. Rep. of Germany | 73/61.4 |
| 721410 | 11/1966 | Italy . | |
| 2048836 | 12/1980 | United Kingdom . | |
| 2116319 | 9/1983 | United Kingdom | 73/61.4 |

Primary Examiner—Stewart J. Levy
Assistant Examiner—Joseph W. Roskos
Attorney, Agent, or Firm—Joseph W. Molasky & Assocs.

[57] ABSTRACT

In an apparatus for measuring the rate of erythrosedimentation of the blood a bell mouthed test tube is provided, having a cylindrical part in which a calibrated and graduated sealing tube, topped with an overflow sleeve for the excess blood, slides. This overflow sleeve allows an automatic filling with blood of the calibrated tube independently from the care taken in the filling of the tapered test tube.

9 Claims, 7 Drawing Figures

APPARATUS FOR MEASURING THE RATE OF ERYTHROSEDIMENTATION OF THE BLOOD

Many different apparatuses are known for measuring the rate of erythrosedimentation of the blood (Katz factor).

One known method in the determination of the rate of erythrosedimentation (E.S.R.) is the Westergren method.

The blood obtained from venopuncture is immediately mixed in the proportion of 4 volumes of blood to 1 of Sodium Citrate. The blood is introduced in a calibrated tube which is placed in a vertical position in a suitable support. After the first and the second hour, the height of the formed plasmatic column is read.

In Italian Pat. No. 721.410, compare parent U.S. Pat. No. 3,373,601 and G.B. Pat. No. 2.048.836, the oral aspiration of the blood is obviated by manufacturing the test tube with an internal sealing rim which cooperates in the manner of a piston gasket with the blood of the graduated tube. The graduated tube receives blood from the test tube leaving an air space in such a way that, by adjusting the volume of the air space, it is possible to bring the blood level to zero (0), (having made the tube touch the bottom of the test tube). It will be understood that such a method has different inconveniences both in the moulding and in function, for the stated reason that adjusting operations are necessary in order for the level of the blood to reach, with its meniscus, the zero (0) reference graduation.

The object of the invention is to reduce or obviate in a practical way the above mentioned inconveniences by proposing an apparatus for measuring the rate of erythrosedimentation (E.S.R.) of the blood, characterized in that it comprises a test tube (PR) having a cylindrical portion (PC$^1$), a calibrated tube (TC) dimensioned to be a sliding and sealing fit in the cylindrical portion (PC$^1$) of the test tube (PR), the top of said calibrated tube (TC) being provided with an overflow sleeve (BS) for receiving, in use, excess blood from the test tube.

An embodiment of apparatus according to the invention will now be described by way of example with reference to the accompanying drawings, in which.

Figure 1:
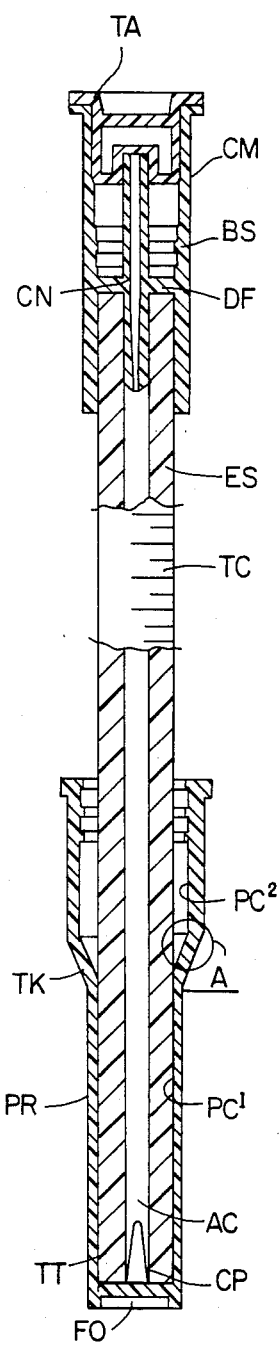
FIG. 1 represents in detailed longitudinal section the various elements of the apparatus according to the invention.
Figure 3:
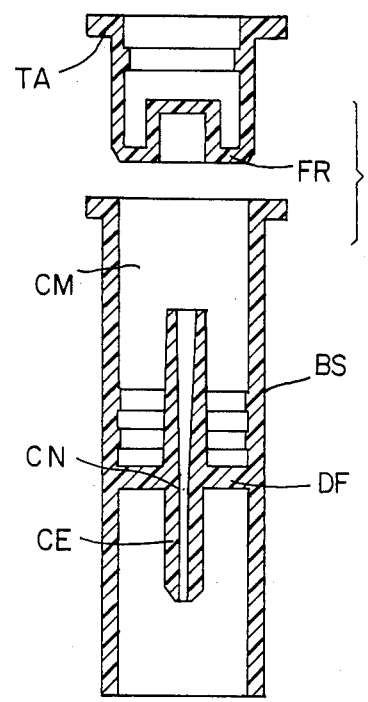
FIG. 3 represents an enlarged, sectional view of the sleeve of FIG. 1.

With reference to the drawings, PR indicates a test tube of transparent plastic material having a perfectly cylindrical part PC$^1$ which prolongs itself with another cylindrical part PC$^2$ of greater diameter. The two portions adjoin in correspondence of a conical trunk part TK with a knurled border ZR which in one way acts as a reference line and in another way permits to obviate the blood surface tension so as to facilitate the mixing of blood/anticoagulant.

TC indicates a graduated and calibrated tube hereinafter mentioned as "pipette" also made of transparent plastic material, the external diameter of which is such that it will slide and seal along the cylindrical part PC$^1$.

The pipette is, preferably, perfectly, transparent, without visible defects or internal striations.

The graduated scale in mm. extends for 150±0.35 mm. from one extremity to the other of the vertical axis.

Generally, the test tube PR is filled in advance with an anticoagulant AC and closed with a stopper TP of flexible material in such a way to permit an hermetic sealing of the test tube.

According to a very important characteristic of the invention, a sleeve BS is provided which is mounted and sealed in correspondence of the extremity ES of the pipette and presents a small canal CN which projects out in respect to a diaphragm DF in such a way that it extends on one side in the tube (pipette) and on the other in a chamber CM forming an excess overflow tank.

The apparatus functions as follows:

First of all the stopper TP is removed (or pierced) and then the test tube PR is filled with blood up to the knurled zone ZR; the filling is executed with some approximation in excess for reasons which will emerge further on. The calibrated tube (pipette) TC is then introduced in the part PC$^1$ and consequently the blood will rise up inside said pipette.

Supposing, as is verified in the majority of the cases, that the volume of the blood is greater than the internal volume of the pipette, the excess blood will flow through the canal CN and it will be deposited in the chamber CM assuring, for this reason, a constant level of blood independently of the care taken in filling with the blood the test tube PR. In fact, after the simple operation of introducing the pipette TC all the way down until it is arrested by the bottom FO of the test tube, an operator does not have to execute any other operation or adjustment and this is positively reflected not only in the exactness of the measurement of the rate of erythrosedimentation, but also in the rapidity of the measure itself.

It is observed that the test tube does not have any sealing rim. Therefore, the manufacturing or moulding requirements are remarkably simplified and every moulding tolerance (pipette calibration) is practically compensated by the excess overflow sleeve BS.

It is also observed that the filling of the test tube with blood is not critical.

In the case of a great excess of blood, the bell mouthed part PC$^2$ of the test tube serves as an excess blood tank without affecting the accuracy of the measurement in as much that the blood which flows into the calibrated tube (pipette) is always the same volume as the internal portion PC$^1$ thanks to the continuous seal of the pipette along the portion PC$^1$.

The overflow sleeve will be manufactured in a plastic material so as to be mounted on the calibrated tube (pipette) and will be constituted of materials not necessarily transparent.

In order to prevent excess blood from being sprayed externally with the risk of contaminating the room, the overflow sleeve can be provided with a cap TA which has a hole FR so as to prevent the "cap" function from negatively affecting the value of the measure.

The cap TA can be connected to the overflow sleeve by means of an isthmus so as to form a single unit.

According to an important characteristic, the diameter of the entrance cone CE of the sleeve is proportioned in such a way that it may intercept the flow of the erythrocytes and function as a barrier for the same, that cannot longer influence the value of the measure.

Figure 6:
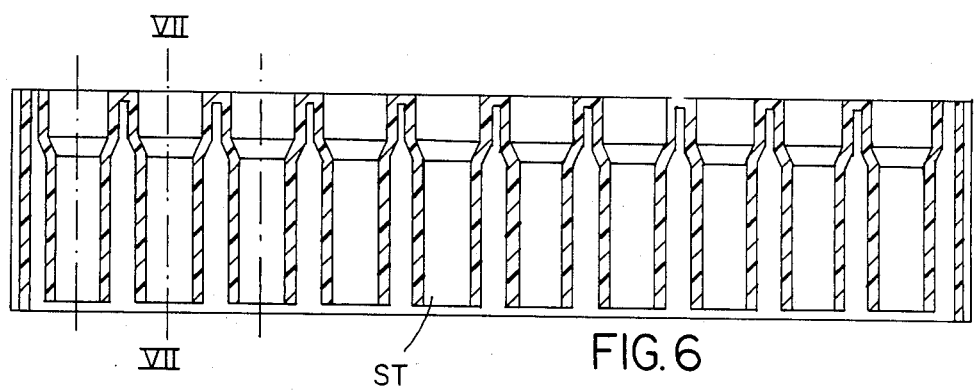
FIGS. 6 and 7 represent in longitudinal and transverse section (VII—VII of FIG. 6) a base for the support of the measuring apparatus.
Figure 7:
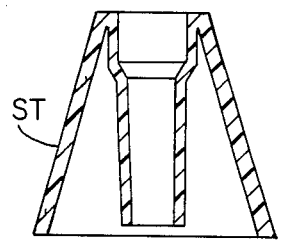

As seen from FIG. 6, a stand ST in a transparent plastic material is provided in which the test tubes PR are received and kept in a vertical position, and touching the work bench top when inserted in the stand.

Figure 4:
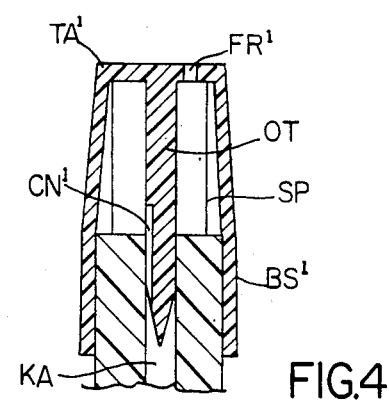
FIG. 4 represents a variation of the overflow sleeve embodying the cap.
Figure 2:
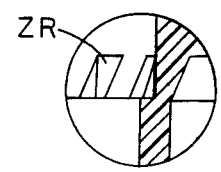
FIG. 2 represents the part A of FIG. 1.
Figure 5:
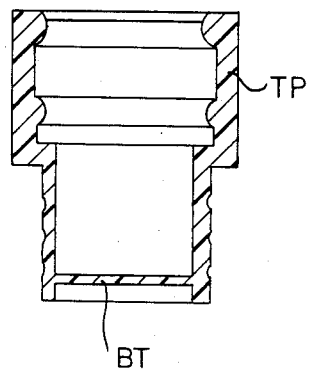
FIG. 5 represents in section the stopper of the test tube.

The concept of the invention can also be expressed according to the variation of FIG. 4. In this realization the overflow sleeve $BS^1$ presents an obturator OT which cooperates with the canal KA of the pipette, said obturator being completed with a milling $CN^1$ equivalent to the canal KA and proportioned in such a way as to prevent the reflux of the blood. The sleeve presents a vent hole $FR^1$ and its bottom $TA^1$ functions as a cap (anti-spray). The sleeve presents some arrest counter shoulders SP in a rib formation.

The test tube may be filled with blood without removing the cap TP: in effect as provided by the same Applicant in Italian Patent Application No. 30952 A/76 filed on 29th Dec. 1976, the bottom BT of the cap TP may be of perforable kind and the end of the calibrated tube test tube to the "zero" location may be tapered TT in order to secure a prompt perforation. The bottom portion FO of the test tube may be provided with a conical projection CP in order to secure a tight obturation of the calibrated tube with the cylindrical portion of the tube, thus obviating possible moulding deficiencies.

We claim:

1. Apparatus for measuring the rate of erythrosedimentation characterized in that it comprises a test tube (PR) having a cylindrical portion ($PC^1$), a calibrated tube (TC) (pipette) dimensioned to be a sliding and sealing fit in the cylindrical portion ($PC^1$) of the test tube (PR), the top of said calibrated tube (TC) being provided with an overflow sleeve (BS) for receiving, in use, excess blood from the test tube.

2. Apparatus according to claim 1, in which the open end of the test tube (TC) is provided with a tapered portion (TK) of increasing dimension.

3. Apparatus according to claim 2, in which the test tube (TC) is provided as an extension of the tapered portion with a second cylindrical portion ($PC^2$) of greater cross-sectional dimension than the first cylindrical portion ($PC^1$).

4. Apparatus according to claim 2, characterized by the fact that said sleeve comprises a cap which can be forced on the extremity of the calibrated tube (pipette) and provided with an overflow canal (CN) which on one side can receive blood from the calibrated tube (pipette) and on the other side projects out into an excess blood reception tank therefore ensuring an automatic filling and zero levelling of the calibrated tube.

5. Apparatus according to claim 4, in which the overflow canal presents an entrance cone with an internal diameter inferior to the diameter of the blood erythrocyte.

6. Apparatus according to claim 4, in which the overflow sleeve ($BS^1$) comprises a cap provided with an air vent hole and extending with an obturator (OT) of the reflux of blood cooperating with the longituninal hole of the calibrated tube (pipette) and provided with a milling ($CN^1$) so as to prevent the reflux of the erythrocytes.

7. Apparatus according to claim 4, characterized by the fact that it is provided with a knurled corona made to neutralize the blood surface tension.

8. Apparatus according to claim 4, wherein the bottom portion of the test tube is formed with a conical projection operating as obturator means with the canal.

9. Apparatus according to claim 1, in which the sleeve is provided with an anti-spray cap and a vent hole for the air.

* * * * *